(12) United States Patent
Eidenberger

(10) Patent No.: US 7,812,198 B2
(45) Date of Patent: Oct. 12, 2010

(54) PROCESS FOR THE MANUFACTURE OF A COMPOSITION CONTAINING AT LEAST ONE XANTHOPHYLL

(75) Inventor: Thomas Eidenberger, Steyr (AT)

(73) Assignee: OMNICA GmbH, Hamburg (DE)

( * ) Notice: Subject to any disclaimer, the term of this patent is extended or adjusted under 35 U.S.C. 154(b) by 103 days.

(21) Appl. No.: 12/294,202

(22) PCT Filed: Mar. 1, 2007

(86) PCT No.: PCT/AT2007/000104

§ 371 (c)(1),
(2), (4) Date: Sep. 23, 2008

(87) PCT Pub. No.: WO2007/098520

PCT Pub. Date: Sep. 7, 2007

(65) Prior Publication Data

US 2009/0118379 A1    May 7, 2009

(30) Foreign Application Priority Data

Mar. 2, 2006    (AT)    ................................ A 356/2006

(51) Int. Cl.
*C07C 35/18* (2006.01)
(52) U.S. Cl. .................................................... 568/816
(58) Field of Classification Search ........................ None
See application file for complete search history.

(56) References Cited

U.S. PATENT DOCUMENTS

| | | | |
|---|---|---|---|
| 3,891,504 A * | 6/1975 | Schocher et al. | ............... 435/67 |
| 4,211,577 A | 7/1980 | Wallin | |
| 4,302,200 A | 11/1981 | Yokoyama et al. | |
| 4,921,475 A | 5/1990 | Sibalis | |
| 5,008,110 A | 4/1991 | Benecke et al. | |
| 5,087,240 A | 2/1992 | Sibalis | |
| 5,088,977 A | 2/1992 | Sibalis | |
| 5,163,899 A | 11/1992 | Sibalis | |
| 5,164,189 A | 11/1992 | Farhadieh et al. | |
| 5,200,186 A | 4/1993 | Gabetta et al. | |
| 5,254,346 A | 10/1993 | Tucker et al. | |
| 5,290,561 A | 3/1994 | Farhadieh et al. | |
| 5,336,168 A | 8/1994 | Sibalis | |
| 5,352,213 A | 10/1994 | Woodard | |
| 5,382,714 A | 1/1995 | Khachik | |
| 5,407,713 A | 4/1995 | Wilfong et al. | |
| 5,523,494 A | 6/1996 | Torres-Cardona et al. | |
| 5,648,564 A | 7/1997 | Ausich et al. | |
| 5,780,693 A | 7/1998 | Bernhard et al. | |
| 5,817,354 A | 10/1998 | Mozaffar et al. | |
| 5,912,363 A | 6/1999 | Nafisi-Movaghar et al. | |
| 6,221,417 B1 | 4/2001 | Sas et al. | |
| 6,262,284 B1 | 7/2001 | Khachik | |
| 6,313,169 B1 | 11/2001 | Bowen et al. | |
| 6,329,557 B1 | 12/2001 | Rodriguez et al. | |
| 6,380,442 B1 | 4/2002 | Modhavi et al. | |
| 6,504,067 B1 | 1/2003 | Montoya-Olivera et al. | |
| 2002/0018821 A1 | 2/2002 | Soulier et al. | |
| 2004/0044085 A1 | 3/2004 | Kumar et al. | |
| 2005/0038271 A1 | 2/2005 | Khachik | |
| 2005/0182280 A1 | 8/2005 | Bhaskaran et al. | |

FOREIGN PATENT DOCUMENTS

| | | |
|---|---|---|
| DE | 198 18 563 | 4/1998 |
| EP | 1 325 943 | 7/2003 |
| JP | 2003/238442 | 8/2003 |
| WO | WO 98/45241 | 10/1998 |
| WO | WO 2006/002735 | 1/2006 |

OTHER PUBLICATIONS

International Search Report PCT/AT2007/000104 (2 pgs.).

* cited by examiner

*Primary Examiner*—Brian J Davis
(74) *Attorney, Agent, or Firm*—Scott D. Rothenberger; Fulbright & Jaworski

(57) ABSTRACT

The present invention relates to a process for the manufacture of a composition containing at least one xanthophyll selected from the group consisting of lutein and zeaxanthin, said process comprising the steps of providing an extract of Marigold flower containing the xanthophyll(s) in esterified form; saponifying the Marigold flower extract and isolating the xanthophyll(s). The process according to the invention is characterized in that the step of saponifying the Marigold flower extract is carried out in the presence of a quaternary ammonium base.

22 Claims, No Drawings

PROCESS FOR THE MANUFACTURE OF A COMPOSITION CONTAINING AT LEAST ONE XANTHOPHYLL

CROSS-REFERENCE TO RELATED APPLICATION

This Application is a Section 371 National Stage Application of International Application No. PCT/AT2007/000104, filed 1 Mar. 2007 and published as WO 2007/098520 A1 on 7 Sep. 2007, which claims the priority from the Austrian application A 356/2006, filed 2 Mar. 2006, the subject matter of which are hereby incorporated by reference in its entirety.

The present invention relates to a process for the manufacture of a composition at least one xanthophyll selected from the group consisting of lutein and zeaxanthin.

Xanthophylls are yellow pigments of the oxycarotenoid type, from the carotenoid group. The group of xanthophylls is composed of lutein, zeaxanthin, and $\alpha$- and $\beta$-cryptoxanthin.

Lutein is a carotenoid of the formula

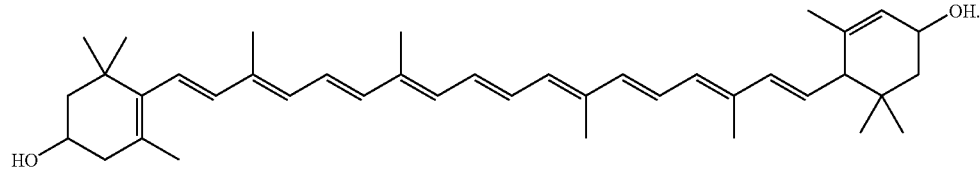

Zeaxanthin, a carotenoid of the formula

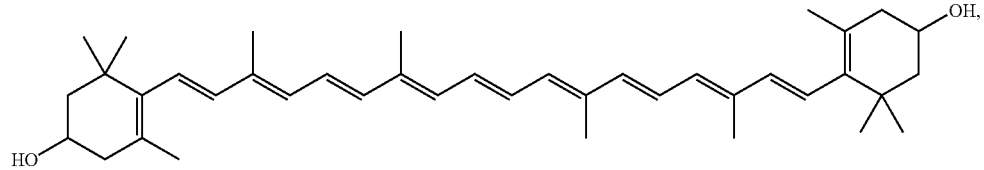

is an isomer of lutein.

Xanthophylls are reported to have activity against cancer, cardiovascular and eye diseases. Therefore, it is widely known to use extracts containing xanthophylls as a nutrient, especially as a food ingredient.

It is known to isolate lutein from the extract of Marigold flower, where lutein is present in an esterified form, via saponification of the extract.

For example, U.S. Pat. No. 5,382,714 A, U.S. Pat. No. 5,648,564 A, U.S. Pat. No. 6,504,067 B and US 2005/0182280 A disclose details of the various steps of this process, involving obtaining an extract from Marigold containing lutein in its ester form, saponifying the extract in order to obtain the alcohol form of lutein, and isolating lutein.

In most of these processes, lutein is obtained in a mixture with other components, especially zeaxanthin. However, the amount of zeaxanthin in the mixture is low.

A process for the isomerization of lutein to zeaxanthin is disclosed in U.S. Pat. No. 5,523,494 A. According to this document's references to prior art, it is known to obtain zeaxanthin by isomerizing lutein in a reaction catalyzed with sodium ethoxide in the presence of ethanol and benzene, or from lutein using potassium methoxide in the presence of methanol and dimethylsulfoxide.

According to the process disclosed in U.S. Pat. No. 5,523,494, lutein extract is treated at 25° C. to 180° C. with a strongly alkaline aqueous solution. As a result, the zeaxanthin content in the mixture is increased. The maximum amount of zeaxanthin according to the examples section, however, is only 24.0%.

For several applications, it is desirable to have xanthophyll compositions containing zeaxanthin in a higher amount than previously disclosed. Furthermore, it would be desirable to be in a position to control the ratio of lutein and zeaxanthin when preparing xanthophyll containing compositions from extracts of Marigold flower.

The present invention solves these problems by means of a process for the manufacture of a composition containing at least one xanthophyll selected from the group consisting of lutein and zeaxanthin, comprising the steps of providing an extract of Marigold flower containing the xanthophyll(s) in esterified form saponifying the Marigold flower extract and isolating the xanthophyll(s), which is characterized in that the step of saponifying the Marigold flower extract is carried out in the presence of a quaternary ammonium base.

It has surprisingly been found that the presence of a quaternary ammonium base in the step of saponifying the Marigold flower extract increases the amount of zeaxanthin in the resulting xanthophyll mixture. Furthermore, by way of appropriately adjusting the amount of quaternary ammonium added, it is possible to control the ratio of zeaxanthin to lutein in the resulting mixture.

US 2005/0182280 discloses a process wherein a phase transfer catalyst is used during the saponification step of the Marigold flower extract. Quaternary ammonium salts are mentioned there as possible phase transfer catalysts.

In contrast thereto, the present invention employs a quaternary ammonium base, which apparently acts as an isomerization catalyst.

Furthermore, according to US 2005/1082280, the temperature of the saponification reaction is should be quite low, such as at 45° C. However, when carrying out the saponification reaction under the conditions disclosed in US 2005/0182280, it was not possible to achieve substantial saponification of the xanthophyll esters.

In the process according to the invention, the quaternary ammonium base employed during the saponification step preferably has the general formula I

wherein $R_1$ is selected from the group consisting of optionally substituted aryl and linear or branched alkyl with 1 to 18 C-atoms, and $R_2$, $R_3$, $R_4$ independently from each other are alkyl with 1 to 6 C-atoms.

In an especially preferred embodiment of the present invention, the quaternary ammonium base is preferably selected from the group consisting of hexadecyltrialkylammonium hydroxides, preferably hexadecyltrimethylammonium hydroxide, and benzyltrialkylammonium hydroxides, preferably benzyltrimethylammonium hydroxide.

As already mentioned above, it has been found that it is possible to adjust the ratio of zeaxanthin to lutein in the final product by varying the amount of quaternary ammonium base employed in the saponification step. In the case of using hexadecyltrimethylammonium hydroxide, for example, the preferred molar ratio of quaternary ammonium base to the lutein present in the Marigold flower extract (the various lutein esters contained in the extract are calculated as lutein), ranges from 0.5:1 to 23:1. The higher the molar ratio of quaternary ammonium base to the lutein is, the higher is the content of zeaxanthin in the resulting mixture.

Therefore, by means of the process according to the invention, it is possible to control the ratio between lutein and zeaxanthin in the resulting xanthophyll mixture: In this regard, it was also found that, in addition to the presence of the quaternary ammonium base according to the invention, apparently the duration of the saponification reaction is decisive for the degree of isomerization from lutein to zeaxanthin: The longer the reaction is carried out, the more zeaxanthin results.

In the process according to the invention, the saponification step may be carried out as known per se by treatment of the Marigold flower extract with alkali hydroxide in an alcoholic solution.

Preferably, the alkali hydroxide employed is NaOH and the alcohol is ethanol. Preferably, anhydrous ethanol may be used.

The saponification step may be carried out at a temperature of from 70° C. to 80° C.

In order to obtain the Marigold flower extract used in the saponification step, extracting Marigold flower with a solvent selected from the group consisting of alkanes, preferably hexane, and petroleum ether, may be carried out as known per se.

In order to isolate the product of the saponification step, a process comprising the stages of
  diluting the saponification mixture with water
  filtering the diluted mixture
  isolating, washing and drying the solid residue
may be employed.

A further preferred embodiment of the process according to the present invention comprises the further step of mixing the isolated xanthophyll(s) with a plant oil, such as soybean oil, and vitamin C and heating the mixture under reduced pressure.

It is known to mix the isolated product of the saponification with products such as soybean oil and vitamin C in order to stabilize the obtained xanthophylls. By heating the obtained mixture under reduced pressure, the residual amount of the solvent used for obtaining the Marigold flower extract, such as hexane, can be further reduced.

The present invention, in one further aspect, relates to a composition containing at least one xanthophyll selected from the group consisting of lutein and zeaxanthin, obtainable by the process according to one of the preceding claims.

Especially, the composition according the present invention may contain zeaxanthin in a weight ratio to lutein of more than 1:1, i.e. in much higher amounts than e.g. disclosed in U.S. Pat. No. 5,523,494 A. It is even possible to obtain compositions with a weight ratio of zeaxanthin content to lutein content of 9:1 or more, up to a point where essentially only zeaxanthin is present as a xanthophyll component in the composition.

The composition according to the present invention may preferably contain both lutein and zeaxanthin.

In the following, the present invention is explained in more detail by way of examples of preferred embodiments:

EXAMPLE 1

Step 1

Extraction

For extracting xanthophylls in their esterified form from Marigold flower, a conventional solvent such as hexane or petroleum ether is employed. The quantity of solvent may be 8 times the weight of the Marigold flower. Extraction is carried out two times at 60° C.+/−2° C. The combined extraction solution is concentrated at 70° C.+/−3° C. under reduced pressure. After recovering the solvent, a concentrated extract is obtained. The amount of lutein diester in the concentrated paste is around 15% according to UV analysis.

Step 2

Saponification

The concentrated paste obtained in step 1 is saponified employing the following conditions:
The ratio of concentrated paste to saponifying agent (NaOH) and solvent (ethanol) is around 50/35/250 concentrated paste/NaOH/ethanol.
The saponification process is carried out at 75° C.+/−3° C. under stirring for around three hours.

Step 3

Isolation

After the saponification reaction is completed, 15 times (compared to weight of concentrated paste) of hot water at a temperature of 80° C. is added into the reaction mixture. The solution is stirred around three minutes, then it is filtered. Preferably, a bigger diameter filter is used in order to have quick filtration.

Afterwards, hot water is used to wash the crystals in order to improve the purity of the product. The xanthophyll crystals on filter are dried at 80° C.+/−2° C. under vacuum. The drying time is around 5 hours, and the water content should be less than 8%. After drying, it is found by HPLC analysis that the lutein content is 88% min, and that the zeaxanthin content is 6.1% min. The total content of carotenoids in the product is 94% min.

In order to prepare a product with a low residual amount of solvent, the dried powder is sieved and then added in a certain amount of soybean oil and a small quantity of Vitamin C.

A colloid mill-machine is used to obtain a homogeneous suspension of the xanthophyll mixture in the soybean oil. This suspension is transferred to another reactor, and nitrogen is fed in with a speed of 150 ml/min under vacuum (less than 10 mm Hg). The suspension is heated at 85° C.+/−2° C. for around 3 hours. The residual amount of solvents in the product is reduced to less than 5 ppm.

EXAMPLE 2

Using an alkane-type solvent with a boiling point of 70~90° C., Marigold flower is extracted three times for two hours each. The quantity of solvent is 8 times the weight of Marigold flower. 15 g concentrated paste is obtained after concentrating the combined extracted solution, based on 200 grams of marigold flower. The content of lutein diester is 14.6% (UV).

EXAMPLE 3

50 g of the concentrated paste obtained according to example 2 is transferred to a reactor. 250 ml ethanol, 35 grams NaOH and 50 ml water are added. The reaction is carried out at 75° C. for 4 hours. After completion of the reaction, 800 ml hot water (80° C.) are added into reaction solution under stirring for two minutes. The solution is filtered. The solid residue on the filter is dried at 80° C. under reduced pressure for 5 hours. 5.0 g solid is obtained. The lutein content of the product is 88.5% (HPLC), and the zeaxanthin content is 6.3% (HPLC). The total amount of carotenoids is found to be 95% (UV), the water content is 6.7%.

EXAMPLE 4

50 g concentrated paste obtained according to example 2 is transferred to a reactor. 35 grams NaOH and 200 ml ethanol solution containing 38% (w/v) benzyl trimethyl ammonium hydroxide are added. The reaction is carried out at 80° C. under stirring for 5 hours. After completion of the reaction, 700 ml hot water (75~80° C.) are added. The solution is stirred for two minutes and then filtered. The solid residue on the filter is dried at 80° C. under reduced pressure for 4.5 hours. 4.1 grams of yellowish powder are obtained. The lutein content of the product is 5.1% (HPLC) and zeaxanthin content is 90.2% (HPLC). The total amount of carotenoids is 96% (UV), the water content is 7.1%.

EXAMPLE 5

100 g dried lutein powder obtained from example 4 is blended with 300 g soybean oil and 3 g Vitamin C. In a colloid mill, the suspension is grinded until being homogeneous. The suspension is then transferred to another reactor. Nitrogen gas is fed into this reactor at a speed of 150 ml/min under reduced pressure. The suspension is heated to 85° C. for three hours. The solvent content is reduced to 2 ppm after treatment, compared with 450 ppm before treatment.

EXAMPLE 6

150 grams concentrated paste with a content of 13.8% lutein ester are obtained by a similar procedure as that described in example 2.

To 100 grams of this concentrated paste 60 grams NaOH, 300 ml 38% (w/v) benzyl trimethyl ammonium hydroxide ethanol solution and 100 ml water are added in a reactor. The solution is allowed to react while being stirred at 80° C. for 5 hours. After completion of the reaction, 1.400 ml hot water (80° C.) are added into the reactor. The mixture is stirred for 2 minutes and then filtered. The solid residue is dried at 80° C. under vacuum for 4.5 hours. 7.8 grams yellowish powder are obtained. The lutein content of the content is 47% (HPLC), and the zeaxanthin content is 38% (HPLC). The total amount of carotenoids is found to be 89% (UV).

EXAMPLE 7

150 gram concentrated paste with a content of 14.9% lutein as measured via a UV test method (the various lutein esters present in the extract are calculated as lutein) are obtained by a similar procedure as that described in example 2.

To 12.9 g of this concentrated paste, 8.75 g NaOH, and 65 ml of a hexadecyl trimethyl ammonium hydroxide ethanol solution are added in a reactor. The concentration of the hexadecyl trimethyl ammonium hydroxide ethanol solution is varied in order to achieve different molar ratios between ammonium base and lutein contained in the extract. (Tests No. 1-9).

The solution is allowed to react while being stirred at 80 centigrade for 5 hours. After completion of reaction, 1000 ml hot water (80° C.) are added into the reactor. The mixture is stirred for ten minutes and then filtered. The solid residue is washed by 100 ml hot water twice, then dried at 80° C. under vacuum condition for 5 hours. Around 1 gram of yellowish power is obtained. The lutein and zeaxanthin content are tested by HPLC.

The result of the addition of hexadecyl trimethyl ammonium hydroxide ethanol solution in various molar ratios to the lutein contained in the extract are listed in the following table:

TABLE

| Lot No. | Lutein (mol) | Base (mol) | Ratio of base/lutein (mol/mol) | Ratio of zeaxanthin/lutein (w/w) in end product |
|---|---|---|---|---|
| 1 | 0.0033789 | 0.07943 | 23.5076 | 91.00/9.00 |
| 2 | 0.0033789 | 0.07332 | 21.6994 | 94.65/5.35 |
| 3 | 0.0033789 | 0.04154 | 12.2939 | 56.13/43.87 |
| 4 | 0.0033789 | 0.0338 | 10.0033 | 39.60/60.40 |
| 5 | 0.0033789 | 0.01892 | 5.5995 | 22.13/77.87 |
| 6 | 0.0033789 | 0.01775 | 5.2532 | 21.22/78.78 |
| 7 | 0.0033789 | 0.00429 | 1.2696 | 12.43/87.57 |
| 8 | 0.0033789 | 0.00182 | 0.5386 | 11.00/89.00 |
| 9 | 0.0033789 | 0 | 0 | 10.00/90.00 |

The invention claimed is:

1. A process for the manufacture of a composition containing at least one xanthophyll selected from lutein or zeaxanthin, comprising the steps of providing an extract of Marigold flower containing the xanthophyll(s) in esterified form;
saponifying the Marigold flower extract; and isolating the xanthophyll(s),
wherein the step of saponifying the Marigold flower extract is carried out in the presence of a quaternary ammonium base comprising general formula (I)

(I)

wherein $R_1$ is selected from an optionally substituted aryl group or a linear or branched alkyl group with 1 to 18 carbon atoms and $R_2$, $R_3$, $R_4$ each independently, are selected from an alkyl group with 1 to 6 carbon atoms.

2. The process of claim 1, wherein the quaternary ammonium base is a hexadecyltrialkylammonium hydroxide or a benzyltrialkylammonium hydroxide.

3. The process of claim 1, wherein the saponification step is carried out by treatment of the Marigold flower extract with an alkali hydroxide in an alcoholic solution.

4. The process of claim 3, wherein the alkali hydroxide is NaOH and the alcohol is ethanol.

5. The process of claim 1, wherein the saponification step is conducted at a temperature of from 70° C. to 80° C.

6. The process of claim 1, wherein the Marigold flower extract has been obtained by extracting Marigold flower with a solvent comprising an alkane or an alkyl ether.

7. The process of claim 1, wherein the isolation step further comprises the step of
diluting the saponification mixture with water;
filtering the diluted mixture; and
isolating, washing and drying the xanthophyll(s).

8. The process of claim 1, further comprising the step of mixing the isolated xanthophyll(s) with a plant oil and vitamin C and heating the mixture under reduced pressure.

9. The process of claim 2, wherein the hexadecyltrialkyl ammonium hydroxide is hexadecyltrimethylammonium hydroxide or the benzyltrialkylammonium hydroxide is benzyltrialkylammonium hydroxide.

10. The process of claim 6, wherein the alkane is hexane or the alkyl ether is petroleum ether.

11. The process of claim 8, wherein the plant oil is soybean oil.

12. A process to isomerize lutein to zeaxanthin, comprising the steps:
providing an esterified lutein containing composition;
saponifying the esterified lutein containing composition to provide a zeaxanthin containing product; and
isolating the zeaxanthin containing product,
wherein the step of saponifying the esterified lutein containing composition is carried out in the presence of a quaternary ammonium base comprising general formula (I)

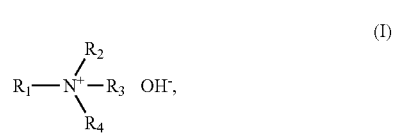
(I)

wherein $R_1$ is selected from an optionally substituted aryl group or a linear or branched alkyl group with 1 to 18 carbon atoms and $R_2$, $R_3$, $R_4$, each independently, are selected from an alkyl group with 1 to 6 carbon atoms.

13. The process of claim 12, wherein the quaternary ammonium base is a hexadecyltrialkylammonium hydroxide.

14. The process of claim 13, wherein the hexadecyltrialkyl ammonium hydroxide is hexadecyltrimethylammonium hydroxide or benzyltrialkylammonium.

15. The process of claim 12, wherein the saponification step is carried out by treatment of the esterified lutein containing composition with an alkali hydroxide in an alcoholic solution.

16. The process of claim 15, wherein the alkali hydroxide is NaOH and the alcohol is ethanol.

17. The process of claim 12, wherein the saponification step is conducted at a temperature of from 70° C. to 80° C.

18. The process of claim 12, wherein the esterified lutein containing composition has been obtained by extracting Marigold flower with a solvent comprising an alkane or an alkyl ether.

19. The process of claim 18, wherein the alkane is hexane or the alkyl ether is petroleum ether.

20. The process of claim 12, wherein the isolation step further comprises the steps of
diluting the saponification mixture with water;
filtering the diluted mixture; and
isolating, washing and drying the zeaxanthin containing product.

21. The process of claim 12, further comprising the step of mixing the isolated zeaxanthin containing product with a plant oil and vitamin C and heating the mixture under reduced pressure.

22. The process of claim 21, wherein the plant oil is soybean oil.

* * * * *